United States Patent [19]

Kurkela et al.

[11] Patent Number: 4,517,198
[45] Date of Patent: May 14, 1985

[54] DIURETIC IMIDAZOLE DERIVATIVES
[75] Inventors: Kauko O. A. Kurkela; Arto J. Karjalainen, both of Oulu, Finland
[73] Assignee: Farmos Group Ltd., Turku, Finland
[21] Appl. No.: 446,717
[22] Filed: Dec. 3, 1982
[30] Foreign Application Priority Data
  Dec. 4, 1981 [GB] United Kingdom ............... 8136646
[51] Int. Cl.$^3$ .................. A61K 31/415; C07D 233/64
[52] U.S. Cl. ..................... 514/400; 548/342; 548/343
[58] Field of Search .............. 548/342; 424/273 R
[56] References Cited
  FOREIGN PATENT DOCUMENTS
  1128524 7/1982 Canada ........................ 548/342
  0009693 4/1980 European Pat. Off. ........... 548/342

OTHER PUBLICATIONS

Chemical Abstracts, 78: 25740q (1973) [Wilkinson, et al., Biochem. Pharmacol. 1972, 21(23), 3187–3192].
Chemical Abstracts, 82: 39231u (1975) [Wilkinson, et al., Pestic. Biochem. Physiol. 1974, 4(3), 299–312].
Yamauchi, O., et al., Chem. Pharm. Bull. 15 (10), pp. 1453–1460, (1967).
Swett, L., et al., J. Med. Chem. 13 (5), pp. 968–970 (1970).
B. N. Craver, et al., Arch. Int. Pharmacodyn., 87, 33–48 (1951).
C. F. Wilkinson, et al., Biochem. Pharm., 21, 3187–3192 (1972).
C. F. Wilkinson, et al., Pesticide Biochem. Phys., 4, 299–312 (1974).

Primary Examiner—Richard A. Schwartz
Attorney, Agent, or Firm—Armstrong, Nikaido, Marmelstein & Kubovcik

[57] ABSTRACT

The invention provides compounds of the formula:

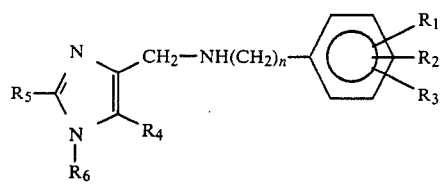

or

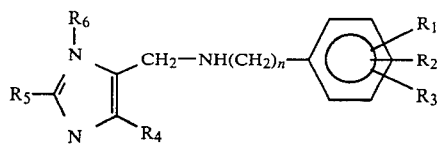

wherein each of $R_1$, $R_2$, $R_3$, $R_4$, $R_5$ and $R_6$ are defined hereinbelow. These compounds exhibit valuable pharmacological activity and are useful in the treatment of mammals, e.g. as diuretic agents. Furthermore, they have antithrombotic and anti-hypertensive effects.

18 Claims, No Drawings

DIURETIC IMIDAZOLE DERIVATIVES

DESCRIPTION

The present invention relates to substituted imidazole derivatives and their non-toxic, pharmaceutically acceptable acid addition salts, and their preparation, to pharmaceutical compositions containing the same, and to their use.

The imidazole derivatives of the present invention have the general formula:

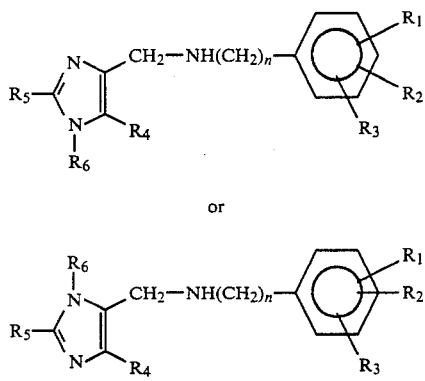

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or a substituted or unsubstituted benzyl group; and n is 0 or 1. Mention may be made of compounds in which $R_1$, $R_2$ and $R_3$ are the same or different and are hydrogen, chloro, bromo, methyl, ethyl, methoxy or hydroxy and, more preferably, $R_1$ is hydrogen, chloro, bromo, methyl, ethyl, or methoxy and each of $R_2$ and $R_3$, which are the same or different, is chloro, bromo, methyl, ethyl, methoxy or hydroxy.

The non-toxic pharmaceutically acceptable acid addition salts of these compounds are also within the scope of the invention.

The compounds of the formula (I) form acid addition salts with both organic and inorganic acids. They can thus form many pharmaceutically usable acid addition salts, as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one of the compounds of formula (I) or a non-toxic, pharmaceutically acceptable salt thereof, and a compatible pharmaceutically acceptable carrier therefor.

The present invention provides, for example, the following specific compounds of formula (I):
4-[α-(2',6'-dichloroanilino)-methyl]-5-methylimidazole
4-[α-(3',5'-dichloroanilino)-methyl]-5-methylimidazole
4-[α-(2',4'-dichloroanilino)-methyl]-imidazole
4-[α-(2',5'-dichloroanilino)-methyl]-imidazole
4-[α-(3',5'-dichloroanilino)-methyl]-imidazole
4-[α-(3',4'-dichloroanilino)-methyl]-imidazole
4-[α-(3'-chloroanilino)-methyl]-imidazole
4-[α-(2',6'-diethylanilino)-methyl]-imidazole
4-[α-(2',6'-dichloroanilino)-methyl]-imidazole
4-[α-(2',6'-dimethylanilino)-methyl]-imidazole
4-[α-(2'-methylanilino)-methyl]-imidazole
4-(α-anilinomethyl)-imidazole
4-[α-(2',3'-dichloroanilino)-methyl]-imidazole
4-[α-(2',4'-dibromoanilino)-methyl]-imidazole
4-[α-(2',3'-dimethylanilino)-methyl]-imidazole
4-[α-(4'-bromoanilino)-methyl]-imidazole
4-[α-(2',6'-dimethylanilino)-methyl]-5-methylimidazole
4-[α-(2',3'-dimethylanilino)-methyl]-5-methylimidazole
4-[α-(2',3'-dichloroanilino)-methyl]-5-methylimidazole
4-[α-(3'-chloroanilino)-methyl]-5-methylimidazole
4-[α-(2',6'-dichloroanilino)-methyl]-2-methylimidazole
4-[α-(2',6'-dimethylanilino)-methyl]-2-methylimidazole
4-[α-(2',3'-dimethylanilino)-methyl]-2-methylimidazole
4-[α-(3'-chloroanilino)-methyl]-2-methylimidazole
4-[α-(2'-methylanilino)-methyl]-2-methylimidazole
4-[α-(2',6'-dichloroanilino)-methyl]-2-ethylimidazole
4-[α-(2',6'-dichloroanilino)-methyl]-1-methylimidazole
4-[α-(2',3'-dichloroanilino)-methyl]-1-ethylimidazole
4-[α-(2',5'-dichloroanilino)-methyl]-1-propylimidazole
4-[α-(3'-chloroanilino)-methyl]-1-benzylimidazole
4-[α-(2',6'-dichloroanilino)-methyl]-3-methylimidazole
4-[α-(2',3'-dichloroanilino)-methyl]-3-ethylimidazole
4-[α-(2',5'-dichloroanilino)-methyl]-3-propylimidazole
4-[α-(3'-chloroanilino)-methyl]-3-benzylimidazole
4-[α-(N-2',6'-dimethylbenzyl)-aminomethyl]-imidazole The compounds of the present invention have been found to possess excellent diuretic properties. Preliminary tests have shown that they also possess other valuable pharmacological properties, for example, antithrombotic and antihypertensive activity.

According to a feature of the invention, the compounds of formula (I) are prepared by reacting an imidazole derivative of the formula

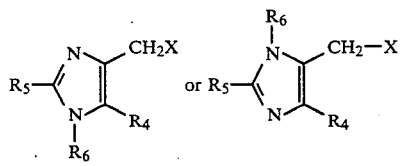

wherein $R_4$, $R_5$ and $R_6$ are as defined before and X is halogen, with a substituted aniline or benzylamine of the formula

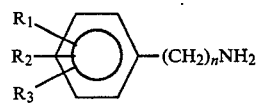

wherein $R_1$, $R_2$, $R_3$ and n are as defined before.

The reaction is carried out in a solvent which may be an alcohol, toluene, xylene or a mixture thereof. The reaction is conveniently performed at a temperature corresponding to the boiling point of the solvent.

Another process for the preparation of compounds of formula (I) comprises reacting an imidazole aldehyde of the formula

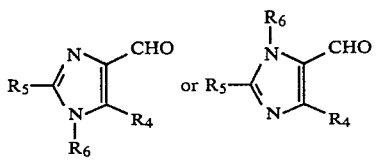

wherein R4, R5 and R6 are as defined above, with a substituted aniline or benzylamine of the formula

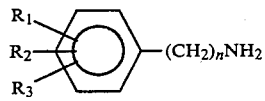

wherein R1, R2, R3 and n are as defined before to give an intermediate of the formula (II)

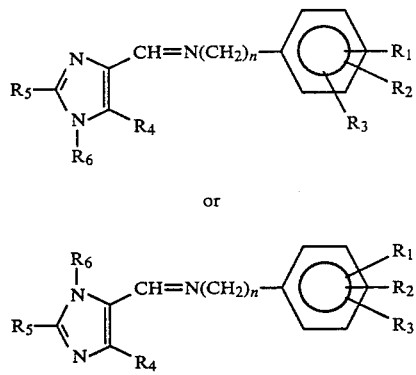

or

The reaction mentioned above is carried out in a solvent, which may be for example toluene or xylene. An acid catalyst, for example toluenesulfonic acid, may be added to the reaction mixture.

In a further stage, the intermediate of formula (II) is reduced to give a compound of formula (I). The reduction can be performed for example as a catalytic hydrogenation, wherein the catalyst may be for example palladium on carbon. Alternatively, the reduction can be carried out with sodium borohydride. Suitable solvents in the reduction stage are for example an alcohol, preferably ethanol, tetrahydrofuran or a mixture of an alcohol and water. The reaction described above can also be performed in one single stage without isolating the intermediate of formula (II).

Yet another process for the preparation of the compounds of formula (I), wherein R6 is hydrogen, comprises hydrogenation of the benzyl group R8—CH2— in a starting material of the formula:

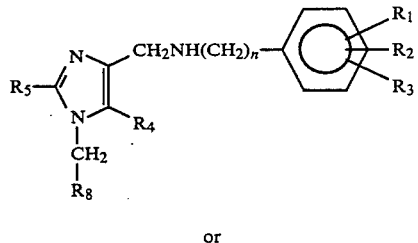

or

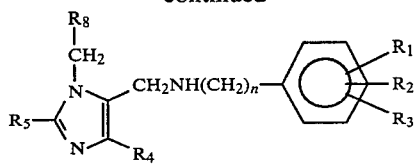

wherein R1, R2, R3, R4, R5 and n are as defined before and R8 is a substituted or an unsubstituted phenyl group. The hydrogenation is conveniently conducted in liquid ammonia with sodium at a low temperature.

A further process for the preparation of the compounds of the formula (I) in which R6 is hydrogen comprises hydrolysing a corresponding compound of the formula:

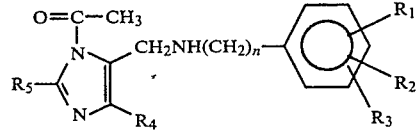

or

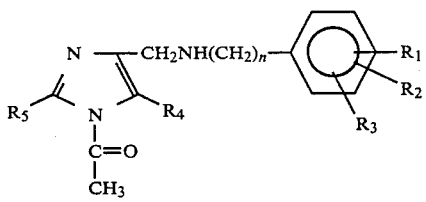

wherein R1, R2, R3, R4, R5 and n are as defined before. Preferably, the hydrolysis is carried out by boiling the starting material, which is an N-acylated imidazole derivative, in an aqueous solution of an inorganic acid until the reaction is completed.

As stated above, the compounds of the general formula (I) and their non-toxic, pharmaceutically acceptable acid addition salts have valuable pharmacological properties and possess diuretic activity. Furthermore they have also proved to possess antithrombotic and antihypertensive activity.

Administration of the isomeric compounds of formula (I), or of their non-toxic, pharmaceutically acceptable acid salts or mixtures thereof may be achieved parenterally, intravenously or orally. Typically, an effective amount of the compound is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative.

The pharmaceutical carriers which are typically employed with the compounds of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The anti-hypertensive properties of the imidazole derivatives of the present invention have been determined by the following procedure. Sprague-Dawley rats of normal weight were first anesthetized with urethane. After this, the femoral artery was connected by way of a polyethylene tube with a blood pressure transducer. The test substance was then injected into the femoral vein and the blood pressure and the pulse frequency were registered with a recorder.

The diuretic activity was studied in rats by collecting the urine output during 0-5 hours after i.p. injection of the compounds. Before the test the animals fasted overnight. They received 10 ml water p.o. immediately before the injection.

The antithrombotic activity was investigated in vitro. The inhibiting activity of the compounds against ADP- and collagen-induced aggregation of thrombocytes was measured. In the test thrombocytes from a cow were used. To 1.2 ml of plasma containing 250000 thrombocytes/mm$^3$ were added 50 μl of a solution of the compound to be tested. After 10 min incubation either ADP or collagen was added. The aggregation of the thrombocytes was turbidimetrically determined at λ=605 nm.

Acute toxicity was determined using female mice of NMRI-Strain with an age of about 7 months and weighing 30-40 g. The administration of the test compound was i.v.

In the antithrombotic activity test the compound 4-[α-(3',5'-dichloroanilino)-methyl]-5-methylimidazole clearly inhibited the collagen-induced and the ADP-induced thrombocyte aggregation. The LD$_{50}$ was 60 mg/kg i.v. in mice.

The compound 4-[α-(2',3'-dichloroanilino)-methyl]-imidazole clearly inhibited the ADP-induced thrombocyte aggregation, but did not inhibit the collagen-induced aggregation. The LD$_{50}$ was 100 mg/kg i.v. in mice.

The compound 4-[α-(2',3'-dichloroanilino)-methyl]-5-methylimidazole, which has a LD$_{50}$ of 60 mg/kg i.v. in mice, clearly inhibited the collagen-induced thrombocyte aggregation.

The compound 4-[α-(2',3'-dimethylanilino)-methyl]-imidazole, which has a LD$_{50}$ of 50 mg/kg i.v. in mice, gave a diuretic effect in rats of 153 percent measured 5 h after administration. The dosage was 0.5 mg/kg. In tests with dogs, this compound has also been found to have diuretic activity.

The compound 4-[α-(2',3'-dimethylanilino)-methyl]-2-methylimidazole, which has a LD$_{50}$ of 80 mg/kg i.v. in mice, showed a diuretic effect in rats of 121% measured 5 h after administration, at a dose of 1 mg/kg.

The compound 4-[α-(2',6'-diethylanilino)-methyl]-imidazole, which has a LD$_{50}$ of 125 mg/kg i.v. in mice, gave a diuretic effect in rats of 146% measured 5 h after administration, at a dose of 4 mg/kg i.p. At a dose of 5 mg/kg perorally, the diuretic effect was found to be 242% (in the rat, measured 5 h after administration).

For the compound 4-[α-(2',6'-dichloroanilino)-methyl]-imidazole having a LD$_{50}$ of 65 mg/kg i.v. in mice, a dose of 0.01-0.3 mg/kg i.v. in the rat gave a 10 percent decrease of the blood pressure measured 20 minutes after administration. In the diuretic test, the same compound caused a diuretic effect of 153% measured 5 h after administration in rats. The dose was 0.1 mg/kg.

The compound 4-[α-(2',6'-dimethylanilino)-methyl]-imidazole, having a LD$_{50}$ of 100 mg/kg i.v. in mice, gave, at a dose of 0.3-3 mg/kg i.v., about 20 percent decrease of the blood pressure and the pulse frequency.

The clinical dosage for the compounds of the invention when administered orally is 0.3-3 mg/kg when used as antithrombotic and diuretic agents and 0.2-2 mg/kg per day when used as antihypertensive agents.

In the Examples below, where $^1$H-NMR or spectrum shifts are presented, the NMR spectra were determined with a Brucker WB 80 DS apparatus using tetramethylsilane or 3-(trimethylsilyl)-propanesulfonic acid sodium salt standard, from which the presented chemical shifts (δ, ppm) are tabulated. The letters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide.

The mass-spectra were determined with a Perkin-Elmer RMU apparatus using direct inlet system. The temperature employed was the lowest temperature needed for the evaporation of the compound as base. In the examples the strongest and the most essential fragment-ions from a structural viewpoint are given as m/e values. In parenthesis is given the intensity of the fragment-ion in relation to the main peak.

The following Examples illustrate the invention.

EXAMPLE 1

4-[α-(2',6'-dichloroanilino)-methyl]-5-methylimidazole

A mixture of 1.7 g of 4-chloromethyl-5-methylimidazole hydrochloride and 4.0 g of 2,6-dichloroaniline is refluxed in 10 ml of ethanol for 3 hours. The solution is then cooled at +5° C. over night. The precipitate is filtered off and washed with cold isopropanol. The yield of the product as hydrochloride is 0.9 g. The ethanol filtrate is evaporated to dryness. The residue is then triturated several times with toluene. Water is added and the mixture is made alkaline (pH 11) with sodium hydroxide. The mixture is extracted with chloroform. The chloroform layer is evaporated to dryness. From the residue the components are separated chromatographically on a column using Giesel Gel and chloroform-ethanol as elutant. In this way a further 1.0 g of product as free base is isolated.

The free base is converted into the hydrochloride in isopropanol-ethylacetate with HCl-ethylacetate. M.p. of the hydrochloride is 183°-185° C. The free base is liberated from the hydrochloride in water with sodium hydroxide. M.p. of the base is 149°-153° C.

$^1$H-NMR (HCl-salt): 1.95 (s, 3H), 4.4 (s, 2H), 4.7 (s, 3H), 6.9-7.4 (m, 3H), 8.5 (s, 1H).

MS: 256 (8%), 254 (11%), 222 (14%), 220 (48%), 163 (75%), 161 (100%), 95 (95%).

EXAMPLE 2

(a)

4-[N-(3',5'-dichlorophenyl)-iminomethyl]-5-methylimidazole 35 ml of toluene, 3.6 g of 5-methyl-4-imidazole aldehyde, 5.4 g of 3,5-dichloroaniline and 0.17 g of p-toluenesulfonic acid are mixed. The mixture is refluxed in connection with a water separator as long as water is removed. Then the mixture is cooled, and the precipitate is filtered off and washed with toluene. The precipitate is 4-[N-(3',5'-dichlorophenyl)-iminomethyl]-5-methylimidazole, m.p. 225°–227° C.

(b) 4-[α-(3',5'-dichloroanilino)-methyl]-5-methylimidazole

The precipitate from the previous stage is dissolved in 20 ml of absolute ethanol. The 1.25 g of sodium borohydride are added in small portions with stirring at room temperature. Stirring at room temperature is continued over-night. 35 ml of water are added and the product is extracted with methylene chloride. From the methylene chloride layer the product is further extracted with gentle warming using 2N hydrochloric acid. The acidic water layer is cooled and the precipitate, which is the hydrochloride of 4-[α-(3',5'-dichloroanilino)-methyl]-5-methylimidazole, is filtered off. It melts at 180°–181° C.

$^1$H-NMR (base): 2.25 (s, 3H), 4.15 (s, 2H), 4.95 (s, 2H), 6.5 (s, 3H), 7.45 (s, 1H).

EXAMPLE 3

4-[α-(2',4'-dichloroanilino)-methyl]-imidazole 35 ml of toluene, 3.2 g of 4-imidazole aldehyde, 5.4 g of 2,4-dichloroaniline and 0.17 g of p-toluenesulfonic acid are mixed. The mixture is refluxed, connected with a water separator, until the theoretical amount of water has been removed. Then the mixture is evaporated to dryness and the residue is dissolved in 20 ml of absolute ethanol. 1.3 g of sodium borohydride are added and the mixture is stirred at room temperature over night. 35 ml of water are added and the product is extracted with methylene chloride. From the methylene chloride layer the product is further extracted with diluted hydrochloric acid and then again with methylene chloride after the water layer has been made alkaline. The methylene chloride extracts are washed with water, dried with Na$_2$SO$_4$ and evaporated to dryness. The residue is crude 4-[α-(2',4'-dichloroanilino)-methyl]-imidazole. This can further be converted to hydrochloride with HCl-ethylacetate in ethylacetate. M.p. of the hydrochloride is 230°–232° C.

The free base is liberated from the hydrochloride in water with sodium hydroxide. M.p. of the base is 118°–120° C.

$^1$H-NMR (base): 3.9 (s, 2H), 4.8 (s, 2H), 6.15–6.8 (m, 4H), 7.2 (s, 1H).

In the Examples 4–24, the procedure of Example 2 or 3 is repeated, except that the corresponding substituted aniline or (in the case of Example 24) benzylamine is used. In Examples 4–16 and 24 the other starting material is 4-imidazole aldehyde. In Examples 17–20 it is 5-methyl-4-imidazole aldehyde, and in Examples 21–23 it is 2-methyl-4-imidazole aldehyde.

EXAMPLE 4

4-[α-(2',5'-dichloroanilino)-methyl]-imidazole

M.p. of the hydrochloride 196°–197° C. M.p. of the base 105°–107° C.

EXAMPLE 5

4-[α-(3',5'-dichloroanilino)-methyl]-imidazole

M.p. of the hydrochloride 189°–191° C. M.p. of the base 129°–132° C.

$^1$H-NMR (base): 3.8 (s, 2H), 4.75 (s, 2H), 6.1 (s, 3H), 6.55 (s, 1H), 7.0 (s, 1H).

EXAMPLE 6

4-[α-(3',4'-dichloroanilino)-methyl]-imidazole

M.p. of the hydrochloride 156°–158° C. M.p. of the base 112°–114° C.

EXAMPLE 7

4-[α-(3'-chloroanilino)-methyl]-imidazole

M.p. of the hydrochloride 156°–158° C. M.p. of the base 74°–84° C.

EXAMPLE 8

4-[α-(2',6'-diethylanilino)-methyl]-imidazole

M.p. of the hydrochloride 184°–188° C. M.p. of the base 89°–92° C.

EXAMPLE 9

4-[α-(2',6'-dichloroanilino)-methyl]-imidazole

M.p. of the hydrochloride 150°–153° C.

EXAMPLE 10

4-[α-(2',6'-dimethylanilino)-methyl]-imidazole

M.p. of the hydrochloride 203°–206° C. (from ethanol).

EXAMPLE 11

4-[α-(2'-methylanilino)-methyl]-imidazole

M.p. of hydrochloride 181°–185° C. M.p. of the base 112°–114° C.

EXAMPLE 12

4-(α-anilinomethyl)-imidazole

M.p. of the hydrochloride 174°–176° C. M.p. of the base 126°–128° C.

EXAMPLE 13

4-[α-(2',3'-dichloroanilino)-methyl]-imidazole

M.p. of the hydrochloride 213°–215° C. M.p. of the base 110°–112° C.

EXAMPLE 14

4-[α-(2',4'-dibromoanilino)-methyl]-imidazole

M.p. of the hydrochloride 222°–224° C. M.p. of the base 153°–154° C.

EXAMPLE 15

4-[α-(2',3'-dimethylanilino)-methyl]-imidazole

M.p. of the hydrochloride 184°–188° C. M.p. of the base 134°–136° C.

EXAMPLE 16

4-[α-(4'-bromoanilino)-methyl]-imidazole

M.p. of the hydrochloride 148°–153° C. M.p. of the base 151°–157° C.

EXAMPLE 17

4-[α-(2',6'-dimethylanilino)-methyl]-5-methylimidazole $^1$H-NMR (base): 2.0 (s, 3H), 2.2 (s, 6H), 4.0 (s, 2H), 5.6 (broad band, 2H), 6.82–7.04 (m, 3H), 7.39 (s, 1H).

EXAMPLE 18

4-[α-(2',3'-dimethylanilino)-methyl]-5-methylimidazole

M.p. of the base 184°–186° C.

EXAMPLE 19

4-[α-(2',3'-dichloroanilino)-methyl]-5-methylimidazole

M.p. of the base 199°–200° C.

EXAMPLE 20

4-[α-(3'-chloroanilino)-methyl]-5-methylimidazole

M.p. of the hydrochloride 181°–183° C. M.p. of the base 164°–168° C.

EXAMPLE 21

4-[α-(2',6'-dichloroanilino)-methyl]-2-methylimidazole

M.p. of the base 130°–134° C.

$^1$H-NMR (base): 2.3 (s, 3H), 4.4 (s, 2H), 6.7–7.4 (m, 4H).

EXAMPLE 22

4-[α-(2',6'-dimethylanilino)-methyl]-2-methylimidazole

M.p. of the base 116°–118° C.

$^1$H-NMR (base): 2.25 (s, 6H), 2.32 (s, 3H), 4.00 (s, 2H), 4.8 (broad band, 2H), 6.65 (s, 1H), 6.76–7.05 (m, 3H).

EXAMPLE 23

4-[α-(2',3'-dimethylanilino)-methyl]-2-methylimidazole

M.p. of the base 183°–186° C.

$^1$H-NMR (base): 2.04 (s, 3H), 2.25 (s, 3H), 2.29 (s, 3H), 4.19 (s, 2H), 4.81 (broad band, 2H), 6.53–7.19 (m, 4H).

EXAMPLE 24

4-[α-(2',6'-dimethylbenzyl)-aminomethyl]-imidazole

M.p. of the hydrochloride 258°–260° C.

$^1$H-NMR (hydrochloride): 2.27 (s, 6H), 4.31 (s, 2H), 4.36 (s, 2H), 4.83 (broad band, 3H), 7.0–7.3 (m, 3H), 7.48 (s, 1H), 7.91 (s, 1H).

We claim:

1. A method of producing in a subject a diuretic, antithrombotic or antihypertensive effect which comprises administering to such subject an effective amount of an imidazole of the formula:

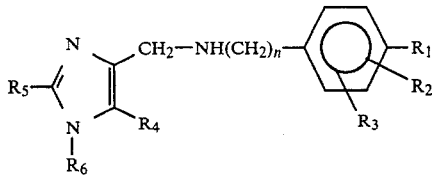

or

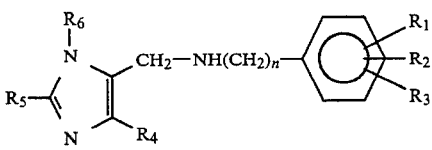

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or a benzyl group; and n is 0 or 1; provided that when n is 0 at least two of $R_1$, $R_2$ and $R_3$ must be other than hydrogen; and further provided that $R_1$, $R_2$ and $R_3$ cannot all be chloro and that two of $R_1$, $R_2$ and $R_3$ cannot be chloro when the third is hydrogen; or a non-toxic pharmaceutically acceptable acid addition salt thereof.

2. A compound according to claim 1 wherein one or more of $R_4$, $R_5$ and $R_6$ is hydrogen.

3. A compound of claim 1 wherein $R_4$, $R_5$ and $R_6$ are all hydrogen.

4. A compound according to claim 1, wherein each of $R_1$, $R_2$ and $R_3$ is hydrogen, chloro, bromo, methyl, ethyl, methoxy or hydroxy.

5. A compound according to claim 1, wherein $R_1$ is hydrogen, chloro, bromo, methyl, ethyl or methoxy and each of $R_2$ and $R_3$ is chloro, bromo, methyl, ethyl, methoxy or hydroxy.

6. A compound according to claim 1 which is 4-[α-(2',6'-diethylanilino)-methyl]-imidazole or a non-toxic pharmaceutically acceptable acid addition salt thereof.

7. A compound according to claim 1 which is 4-[α-(2',6'-dimethylanilino)-methyl]-imidazole or a non-toxic, pharmaceutically acceptable acid addition salt thereof.

8. A compound according to claim 1 which is 4-[α-(2',3'-dimethylanilino)-methyl]-imidazole or a non-toxic, pharmaceutically acceptable acid addition salt thereof.

9. A compound according to claim 1 which is 4-[α-(2',3'-dimethylanilino)-methyl]-2-methylimidazole or a non-toxic, pharmaceutically acceptable acid addition salt thereof.

10. A pharmaceutical composition useful as a diuretic, antithrombotic or antihypertensive agent comprising an effective amount of an imidazole of the formula:

11. A composition according to claim 10 wherein one or more of $R_4$, $R_5$ and $R_6$ is hydrogen.

12. A composition according to claim 10 wherein $R_4$, $R_5$ and $R_6$ are all hydrogen.

13. A composition according to claim 10, wherein each of $R_1$, $R_2$ and $R_3$ is hydrogen, chloro, bromo, methyl, ethyl, methoxy or hydroxy.

14. A composition according to claim 10, wherein $R_1$ is hydrogen, chloro, bromo, methyl, ethyl or methoxy and each of $R_2$ and $R_3$ is chloro, bromo, methyl, ethyl, methoxy or hydroxy.

15. A composition according to claim 10 wherein said imidazole is 4-[α-(2',6'-diethylanilino)-methyl]-imidazole or a non-toxic, pharmaceutically acceptable acid addition salt thereof.

16. A composition according to claim 10 wherein said imidazole is 4-[α-(2',6'-dimethylanilino)-methyl]-imidazole or a non-toxic, pharmaceutically acceptable acid addition salt thereof.

17. A composition according to claim 10 wherein said imidazole is 4-[α-(2',3'-dimethylanilino)-methyl]-imidazole or a non-toxic, pharmaceutically acceptable acid addition salt thereof.

18. A composition according to claim 10 wherein said imidazole is 4-[α-(2',3'-dimethylanilino)-methyl]-2-methylimidazole or a non-toxic, pharmaceutically acceptable acid addition salt thereof.

* * * * *

UNITED STATES PATENT AND TRADEMARK OFFICE
CERTIFICATE OF CORRECTION

PATENT NO. : 4,517,198
DATED     : May 14, 1985
INVENTOR(S) : DIURETIC IMIDAZOLE DERIVATIVES

Page 1 of 2

It is certified that error appears in the above-identified patent and that said Letters Patent is hereby corrected as shown below:

Column 10, line 11:  "compound" should read --method--;
          line 13:  "compound of" should read --method according to--;
          lines 15 and 18:  "compound" should read --method--;
          lines 22, 25, 29 and 33:  "compound according to claim 1 which" should read --method according to claim 1 wherein said imidazole--;
          after line 39 and before line 40 insert:

--
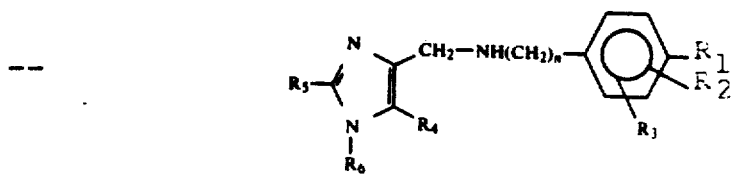

or

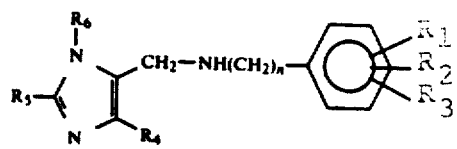

UNITED STATES PATENT AND TRADEMARK OFFICE
CERTIFICATE OF CORRECTION

PATENT NO. : 4,517,198
DATED : May 14, 1985
INVENTOR(S) : DIURETIC IMIDAZOLE DERIVATIVES

It is certified that error appears in the above-identified patent and that said Letters Patent is hereby corrected as shown below:

--wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbon atoms; $R_5$ is hydrogen or a straight or branched alkyl group of 1 to 5 carbon atoms or a phenyl group; $R_6$ is hydrogen or an alkyl group of 1 to 7 carbon atoms or a benzyl group; and n is 0 or 1; provided that when n is 0 at least two of $R_1$, $R_2$ and $R_3$ must be other than hydrogen; and further provided that $R_1$, $R_2$ and $R_3$ cannot all be chloro and that two of $R_1$, $R_2$ and $R_3$ cannot be chloro when the third is hydrogen; or a non-toxic, pharmaceutically acceptable acid addition salt thereof in association with a compatible pharmaceutically acceptable carrier.--

Signed and Sealed this

Seventeenth Day of March, 1987

Attest:

DONALD J. QUIGG

Attesting Officer

Commissioner of Patents and Trademarks